United States Patent [19]

Pagano

[11] 3,996,006

[45] Dec. 7, 1976

[54] SPECIMEN TEST SLIDE

[75] Inventor: Joseph F. Pagano, Paoli, Pa.

[73] Assignee: SmithKline Corporation, Philadelphia, Pa.

[22] Filed: Apr. 28, 1976

[21] Appl. No.: 681,080

[52] U.S. Cl. ............................................. 23/253
[51] Int. Cl.$^2$ ................ G01N 21/06; G01N 31/22
[58] Field of Search ............................ 23/253 TP

[56] References Cited

UNITED STATES PATENTS

| | | | |
|---|---|---|---|
| 3,502,437 | 3/1970 | Mass | 23/253 TP |
| 3,740,196 | 6/1973 | Stroterhoff | 23/253 TP |
| 3,893,808 | 7/1975 | Campbell | 23/253 TP |

*Primary Examiner*—Robert M. Reese
*Attorney, Agent, or Firm*—Smith, Harding, Earley & Follmer

[57] ABSTRACT

A specimen test slide has a front panel and a rear panel. The front panel has a plurality of openings. Sheet means underlie each of these openings for the reception of a specimen. The portion of the sheet under each opening carries a test reagent. A hinged cover overlies the openings. The rear panel has tab means opposite the said openings which are pivotable to expose the underside of the sheet to permit the application of a developing solution. The reagent at each location may be the same or different. When the reagents are different, they can be separately printed on the sheet to underlie different openings. A single sheet is disclosed underlying all of the openings with the employment of a barrier to limit the migration between adjacent portions of the sheet. The use of separate sheets under each opening is also disclosed.

10 Claims, 5 Drawing Figures

SPECIMEN TEST SLIDE

BACKGROUND OF THE INVENTION

It is known to employ specimen slides having a specimen receiving sheet between a front panel and a rear panel with an opening in the front panel and an opening in the rear panel and pivotal covers to cover these openings. Typically, in the case of a test for occult blood in feces, the specimen receiving sheet is paper impregnated with guaiac and a developing solution such as a peroxide solution is applied through the opening in the rear panel.

Frequently it is highly desirable to have two or more specimens for a close side-by-side comparison in the test involved. For example, it is desirable to test more than one portion of a fecal sample when testing for occult blood. At times it is desirable to test a specimen by more than one test, for example, testing a fecal sample by both the guaiac test and the o-tolidine test which have different sensitivities is valuable in the diagnosis for occult blood. The invention provides for the achievement of these objectives.

BRIEF SUMMARY OF THE INVENTION

The invention provides for side-by side comparison testing with the same and different test reagents by providing multiple openings in the front and rear panels with provisions for covering these openings. Advantageously barrier means are provided to prevent migration from one test portion of the slide to another test portion. An entire sheet lying under all openings may carry the test reagent or the sheet may carry the same or different test reagents only in selected portions opposite the openings with the application of the reagent made, for example, by printing. Separate sheets may be employed under the openings with the same or different test reagents being used on the sheets and applied, for example, by printing.

DETAILED DESCRIPTION

Figure 1:
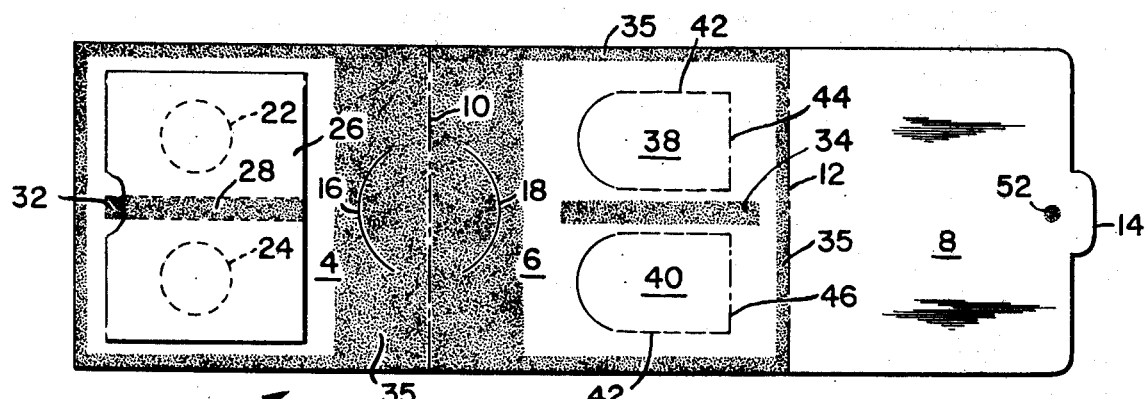
FIG. 1 is a plan view of a partially processed blank for making a slide in accordance with the invention.

A blank 2 formed, for example, from paper or cardboard has a front panel 4, a rear panel 6 and a cover 8. The blank 2 is creased between panels 4 and 6 along the line indicated at 10 to facilitate folding. A crease along the line indicated at 12 between panel 6 and cover 8 facilitates the hinging of cover 8. Cover 8 has a tab 14 which is adapted to pass through circular slit 16 in panel 4 and circular slit 18 in panel 6 to lock the cover in the closed position.

Front panel 4 has a pair of adjacent openings 22 and 24. A sheet of absorbent paper 26, for example, filter paper overlies (as viewed in FIG. 1) openings 22 and 24. Sheet 26 is impregnated with a reagent such as guaiac. A barrier 28 in the central portion of sheet 26 prevents migration of the specimen or a developing solution between the two halves of sheet 26. Barrier 28 may be any material impregnating paper 26 which will prevent migration, for example, glue, a wax or a synthetic resin such as an epoxy, phenolic, polyester or silicone resin commonly used in paper-resin laminates. As illustrated, barrier 28 is formed of glue which is also deposited on the front panel 24 as indicated at 32 and on rear panel 6 as indicated at 34 in order to adhere sheet 26 to both panels 4 and 6. Panels 4 and 6 are adhered together by an adhesive such as glue indicated at 35.

For the application of the developing solution, for example, a peroxide solution, the rear panel 6 is provided with tabs 38 and 40 opposite openings 22 and 24, respectively. Perforations 42 are provided to permit moving the tabs 38 and 40 away from sheet 26 pivoting about crease lines 44 and 46, respectively.

Figure 2:
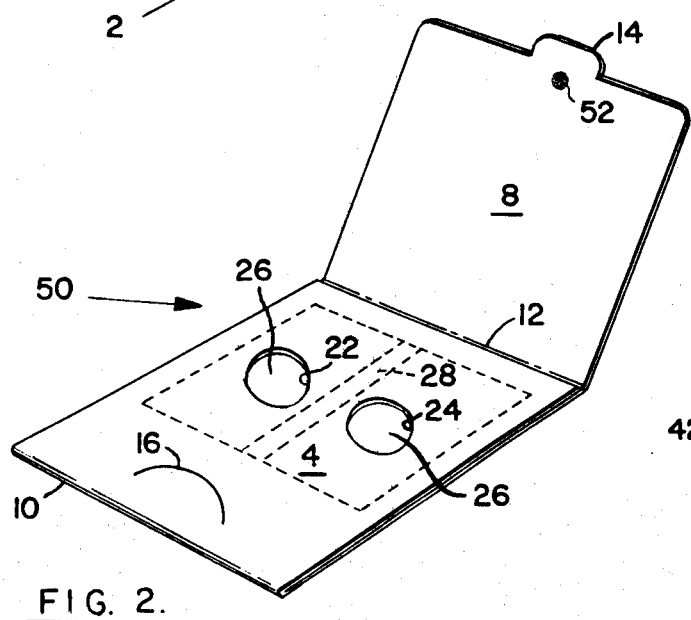
FIG. 2 is a front elevational view of a slide formed from the blank of FIG. 1 with the front cover open.
Figure 3:
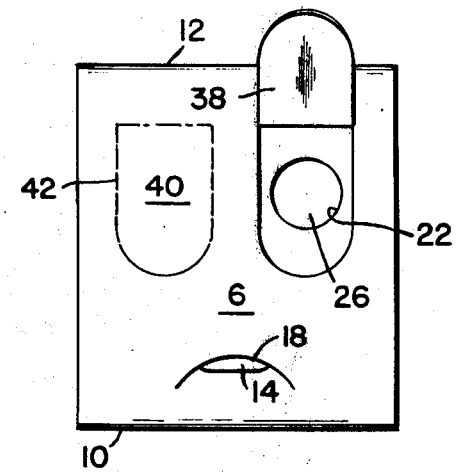
FIG. 3 is a rear view of the slide of FIG. 2 with the front cover closed.

To form the completed slide 50 shown in FIG. 2, blank 2 is folded along crease line 10 to bring panels 4 and 6 together and hold them together principally by the glue at 35. Cover 8 is now hinged about crease 12 and secured to panel 4 by a spot of glue 52.

To use the slide device, the patient separates cover 8 from panel 4 at the spot 52, opens the cover and applies with an applicator a thin smear of a specimen from one portion of his stool on paper 26 through opening 22. He then applies from another portion of his stool a thin smear on paper 26 through opening 24. He then closes the cover locking tab 14 in openings 16 and 18 and returns the slide to his physician. On receiving the slide, the physician pulls tabs 38 and 40 free of rear panel 6 and opens them outwardly. Through the opening thus made the physician applies a peroxide solution on the guaiac impregnated paper 26 opposite each of the openings 22 and 24 and observes the test results, i.e. in the occult blood test the degree to which the color blue is developed. This provides a good side-by-side comparison of test results from two different portions of the patient's stool.

Figure 4:
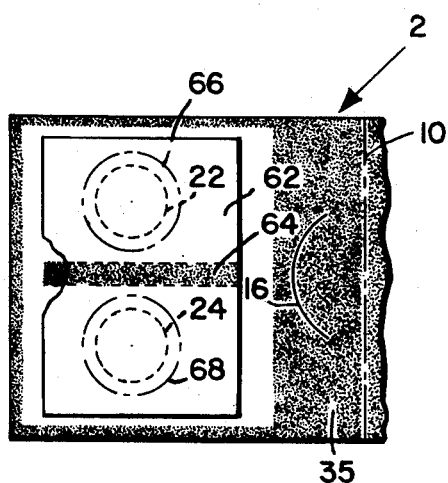
FIG. 4 is a view, partially broken away, of a modified blank for forming a slide.

As shown in FIG. 4, a blank 2 for making a slide in accordance with the invention has secured thereto in lieu of sheet 26 a sheet 62 of paper which has a central glue barrier 64. Sheet 62 differs from sheet 26 in that rather than being impregnated throughout with one reagent, it has printed thereon opposite opening 22 one reagent 66 and it has printed thereon opposite opening 24 a second different reagent 68. Reagent 66 may be, for example, guaiac and reagent 68 may be, for example, o-tolidine. In use the reagents 66 and 68 may be developed with a peroxide or an organic peroxide solution.

Figure 5:
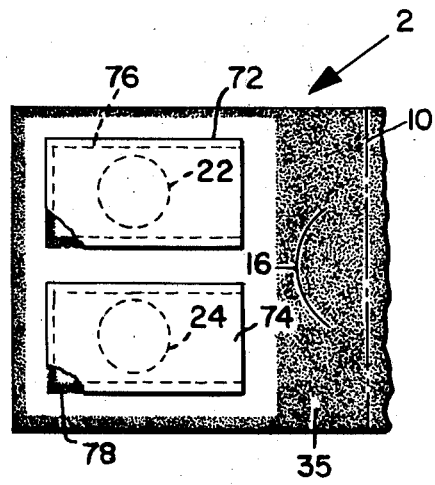
FIG. 5 is a view, partially broken away, of another modified blank for forming a slide employing separate sheets.

As shown in FIG. 5 a blank 2 for use in making a slide in accordance with the invention has a separate sheet 72 opposite opening 22 and a separate sheet 74 opposite opening 24. Sheet 22 may be impregnated with, for example, guaiac and sheet 74 impregnated with, for example, o-tolidine. Sheet 72 is impregnated with epoxy resin indicated at 76 which acts as a barrier and secures sheet 72 to both the front and rear panels. Similarly, sheet 74 is impregnated with epoxy resin 78 which secures sheet 74 to both the front and rear panels.

The above embodiments are illustrative and are not intended to be limiting.

I claim:

1. A specimen test slide comprising:
a front panel,
a rear panel, said front panel having a plurality of openings,
sheet means between the front and rear panels underlying each of said openings for the reception of a specimen and with the portion of the sheet under each opening carrying a test reagent,
a hinged cover adapted to overlie a portion of the front panel and said openings, and
tab means in the rear panel opposite said openings and pivotable to expose the underside of the sheet.

2. The slide of claim 1 in which the sheet means is a single sheet underlying all of the openings and the reagent under each opening is different.

3. The slide of claim 2 in which the sheet has a barrier to prevent the migration of material from the portion of the sheet under one opening to a portion of the sheet under another opening.

4. The slide of claim 1 in which the sheet means is a single sheet underlying all of the openings and the reagent under each opening is the same.

5. The slide of claim 4 in which the sheet has a barrier to prevent the migration of material from the portion of the sheet under one opening to a portion of the sheet under another opening.

6. The slide of claim 5 in which said plurality of openings consists of a pair of adjacent openings.

7. The slide of claim 1 in which the sheet means comprises a separate sheet under each opening.

8. The slide of claim 7 in which at least one of the separate sheets has a reagent different from the reagent on another of the separate sheets.

9. The slide of claim 7 in which each sheet has barrier means to prevent material from passing from the sheet in the direction of an adjacent sheet.

10. The slide of claim 9 in which the plurality of openings consists of a pair of adjacent openings.

* * * * *

Disclaimer 3,996,006.—*Joseph F. Pagano,* Paoli, Pa. SPECIMEN TEST SLIDE. Patent dated Dec. 7, 1976. Disclaimer filed Apr. 13, 1984, by the assignee, *Smithkline Beckman Corp.*

Hereby enters this disclaimer to claims 1 through 10 of said patent.

[*Official Gazette June 12, 1984.*]